(12) United States Patent
Pavlin

(10) Patent No.: US 6,552,160 B2
(45) Date of Patent: Apr. 22, 2003

(54) ESTER-TERMINATED POLY(ESTER-AMIDES) USEFUL FOR FORMULATING TRANSPARENT GELS IN LOW POLARITY FLUIDS

(75) Inventor: Mark S. Pavlin, Savannah, GA (US)

(73) Assignee: Arizona Chemical Company, Jacksonville, FL (US)

( * ) Notice: Subject to any disclaimer, the term of this patent is extended or adjusted under 35 U.S.C. 154(b) by 0 days.

(21) Appl. No.: 09/855,737

(22) Filed: May 14, 2001

(65) Prior Publication Data

US 2002/0187170 A1 Dec. 12, 2002

(51) Int. Cl.$^7$ ............................................. C08G 69/00
(52) U.S. Cl. ................. 528/339.5; 528/289; 528/295.5; 528/300; 528/308; 528/335; 528/347; 424/400; 424/457; 44/275
(58) Field of Search ............................ 528/289, 295.5, 528/300, 308, 335, 339.5, 347; 424/400, 457; 44/275

(56) References Cited

U.S. PATENT DOCUMENTS

| | | | |
|---|---|---|---|
| 2,279,137 A | 4/1942 | Guilfoil, Jr. .................... 67/21 |
| 2,379,413 A | 7/1945 | Bradley .................... 260/404.5 |
| 2,450,940 A | 10/1948 | Cowan et al. ............ 260/404.5 |
| 2,662,068 A | 12/1953 | Floyd ......................... 260/33.6 |
| 2,861,048 A | 11/1958 | Wright et al. ................. 260/22 |
| 3,141,787 A | 7/1964 | Goetze et al. ............... 106/252 |
| 3,148,125 A | 9/1964 | Strianse et al. ................ 167/85 |
| 3,156,572 A | 11/1964 | Carlick et al. ................ 106/27 |
| 3,341,465 A | 9/1967 | Kaufman et al. ............ 252/316 |
| 3,420,789 A | 1/1969 | Wilson ......................... 260/18 |
| 3,595,816 A | 7/1971 | Barrett ......................... 260/18 |
| 3,615,289 A | 10/1971 | Felton ........................... 44/7.5 |
| 3,645,705 A | 2/1972 | Miller et al. ................... 44/7.5 |
| 3,741,711 A | 6/1973 | Bryant ......................... 431/125 |
| 3,819,342 A | 6/1974 | Gunderman et al. .......... 44/7.5 |
| 3,962,122 A | 6/1976 | Trial ........................... 252/392 |
| 4,051,159 A | 9/1977 | Tsoucalas et al. ......... 260/404.5 |
| 4,062,819 A | 12/1977 | Mains et al. .............. 260/18 N |
| 4,066,585 A | 1/1978 | Schepp et al. ............ 260/18 N |
| 4,115,370 A | 9/1978 | Corrado ................. 260/22 CQ |
| 4,128,436 A | 12/1978 | O'Hara et al. .............. 106/243 |
| 4,150,002 A | 4/1979 | Drawert et al. ........... 260/18 N |
| 4,165,303 A | 8/1979 | Schlossman et al. ..... 260/22 D |

(List continued on next page.)

FOREIGN PATENT DOCUMENTS

| | | |
|---|---|---|
| EP | 373878 A2 | 6/1990 |
| EP | 451954 A2 | 10/1991 |
| EP | 470364 A2 | 2/1992 |
| EP | 224389 | 3/1992 |
| EP | 483954 A1 | 5/1992 |
| EP | 527613 A2 | 2/1993 |
| EP | 384208 B1 | 9/1994 |
| EP | 469 435 B1 | 1/1995 |
| EP | 566755 B1 | 6/1996 |
| EP | 467 533 B1 | 11/1997 |
| WO | WO 88/00603 | 1/1988 |
| WO | WO 90/05910 A1 | 5/1990 |
| WO | WO 97/08282 | 3/1997 |
| WO | WO 97/39151 A1 | 10/1997 |
| WO | WO 98/17243 | 4/1998 |
| WO | WO 98/17705 | 4/1998 |
| WO | WO 00/40216 | 7/2000 |
| WO | WO 00/46326 | 8/2000 |
| WO | WO 00/78878 | 12/2002 |

OTHER PUBLICATIONS

Eastman Chemical Company, "Product Information: Eastman 1,4–CHDA–HP (1,4–Cyclohexanedicarboxylic Acid), High Purity," http://www.eastman.com/Product_Information/Product.asp? Product=944 (Accessed Sep. 10, 2001).

Huntsman Corporation, "Jeffamine ® EDR–148 Triethyleneglycoldiamine CAS 929–59–99," Technical Bulletin, 1994, pp. 1–7.

Huntsman Corporation, "Jeffamine ® D–230 Polyoxpropylenediamine [CAS 9046–10–0]," Technical Bulletin, 1997, pp. 1–2.

Huntsman Coporation, "Jeffamine 200 D–400 Polyoxypropylenediamine [CAS 9046–10–0]," Technical Bulletin, 1998, pp. 1–2.

Hunstman Corporation, "Jeffamine® D–2000 Polyoxypropylenediamine [CAS 9046–10–0]," Technical Bulletin, 1994, pp. 1–2.

Huntsman Corporation, "XTJ–502 Poly(oxyethylene)diamine [CAS 65605–36–9]," Technical Bulletin, 1996, pp. 1–2.

Tóth et al., "Analytical Performances of Lipophilic Diamides Based Alkaline Earth Ion–Selective Electrodes," Electoanalysis 5(9–10):781–790, 1993.

Vedanayagam et al., "Kinetics of Reaction of C36 Dimeric Fatty Acids and Ethylenediamine in Solution," J. of Applied Polymer Science 45 (12):2245–2248, Aug. 25, 1992.

Yasuda et al., "Novel Low–Molecular–Weight Organic Gels: N,N,N –Tristearyltrimesamide/Organic Solvent System," Chemistry Letters, pp. 575–576, 1996.

Primary Examiner—Samuel A. Acquah
(74) Attorney, Agent, or Firm—Seed Intellectual Property Law Group PLLC

(57) ABSTRACT

A resin composition is prepared by reacting components comprising dibasic acid, diamine, polyol and monoalcohol, wherein (a) at least 50 equivalent percent of the dibasic acid comprises polymerized fatty acid; (b) at least 50 equivalent percent of the diamine comprises ethylene diamine; (c) 10–60 equivalent percent of the total of the hydroxyl and amine equilvalents provided by diamine, polyol and monoalcohol are provided by monoalcohol; and (d) no more than 50 equivalent percent of the total of the hydroxyl and amine equivalents provided by diamine, polyol and monoalcohol are provided by polyol. This resin composition may be formulated into, for example, personal care products, fragrance releasing products and candles.

31 Claims, No Drawings

U.S. PATENT DOCUMENTS

| | | | |
|---|---|---|---|
| 4,233,170 A | 11/1980 | Genjida et al. | 252/73 |
| 4,259,183 A | 3/1981 | Cadotte | 210/654 |
| 4,275,054 A | 6/1981 | Sebag et al. | 424/65 |
| 4,337,298 A | 6/1982 | Karim et al. | 428/461 |
| 4,341,671 A | 7/1982 | Bolze et al. | 528/324 |
| 4,346,024 A | 8/1982 | Coquard et al. | 524/219 |
| 4,369,284 A | 1/1983 | Chen | 524/476 |
| 4,376,194 A | 3/1983 | Tanaka et al. | 528/288 |
| 4,427,366 A | 1/1984 | Moore | 431/291 |
| 4,438,240 A | 3/1984 | Tanaka et al. | 525/420 |
| 4,449,987 A | 5/1984 | Lindauer | 44/7.5 |
| 4,452,922 A | 6/1984 | Speranza et al. | 521/137 |
| 4,552,693 A | 11/1985 | Hussain et al. | 252/522 A |
| 4,568,270 A | 2/1986 | Marcus et al. | 431/288 |
| 4,571,267 A | 2/1986 | Drawert et al. | 106/27 |
| 4,663,428 A | 5/1987 | Okitu et al. | 528/324 |
| 4,735,746 A | 4/1988 | Speranza et al. | 252/544 |
| 4,742,128 A | 5/1988 | Frisch et al. | 525/424 |
| 4,742,147 A | 5/1988 | Nichols | 528/75 |
| 4,751,272 A | 6/1988 | Okita et al. | 525/398 |
| 4,760,117 A | 7/1988 | Evans et al. | 525/394 |
| 4,769,285 A | 9/1988 | Rasmussen | 428/355 |
| 4,795,581 A | 1/1989 | Nieh et al. | 252/77 |
| 4,816,549 A | 3/1989 | Rumack | 528/336 |
| 4,826,428 A | 5/1989 | Lam | 431/291 |
| 4,830,671 A | 5/1989 | Frihart et al. | 106/27 |
| 4,839,424 A | 6/1989 | Murabayashi | 525/92 |
| 4,855,098 A | 8/1989 | Taylor | 264/103 |
| 4,871,804 A | 10/1989 | Murabayashi | 525/92 |
| 4,889,560 A | 12/1989 | Jaeger et al. | 106/27 |
| 4,914,162 A | 4/1990 | Leoni et al. | 525/420.5 |
| 4,937,069 A | 6/1990 | Shin | 424/66 |
| 4,937,701 A | 6/1990 | Schroder | 362/161 |
| 4,946,922 A | 8/1990 | Reisch et al. | 528/76 |
| 4,946,933 A | 8/1990 | Speranza et al. | 528/339.3 |
| 5,053,484 A | 10/1991 | Speranza et al. | 528/338 |
| 5,069,897 A | 12/1991 | Orr | 424/66 |
| 5,086,162 A | 2/1992 | Speranza et al. | 528/339 |
| 5,091,572 A | 2/1992 | Speranza et al. | 564/139 |
| 5,093,382 A | 3/1992 | Speranza et al. | 521/157 |
| 5,102,656 A | 4/1992 | Kasat | 424/66 |
| 5,118,785 A | 6/1992 | Speranza et al. | 528/347 |
| 5,120,600 A | 6/1992 | Suppiah | 428/323 |
| 5,124,412 A | 6/1992 | Catena et al. | 525/420.5 |
| 5,128,441 A | 7/1992 | Speranza et al. | 528/335 |
| 5,130,382 A | 7/1992 | Speranza et al. | 525/420 |
| 5,132,355 A | 7/1992 | Nahlovsky | 524/474 |
| 5,138,097 A | 8/1992 | Speranza et al. | 564/153 |
| 5,139,677 A | 8/1992 | Pasternak | 210/640 |
| 5,140,097 A | 8/1992 | Speranza et al. | 528/342 |
| 5,143,854 A | 9/1992 | Pirrung et al. | 436/518 |
| 5,177,177 A | 1/1993 | Thullen et al. | 528/339.3 |
| 5,178,646 A | 1/1993 | Barber, Jr. et al. | 51/298 |
| 5,180,802 A | 1/1993 | Hartman et al. | 528/335 |
| 5,191,006 A | 3/1993 | Matsumoto et al. | 524/310 |
| 5,194,638 A | 3/1993 | Frihart et al. | 554/47 |
| 5,214,124 A | 5/1993 | Drawert et al. | 528/335 |
| 5,221,534 A | 6/1993 | DesLauriers et al. | 424/78.03 |
| 5,270,353 A | 12/1993 | Nakano et al. | 523/214 |
| 5,286,288 A | 2/1994 | Tobias et al. | 106/20 B |
| 5,324,812 A | 6/1994 | Speranza et al. | 528/338 |
| 5,338,187 A | 8/1994 | Elharar | 431/288 |
| 5,342,894 A | 8/1994 | Robeson et al. | 525/183 |
| 5,342,918 A | 8/1994 | Howelton et al. | 528/318 |
| 5,350,789 A | 9/1994 | Sagawa et al. | 524/313 |
| 5,364,924 A | 11/1994 | Gerkin et al. | 528/73 |
| 5,372,852 A | 12/1994 | Titterington et al. | 427/288 |
| 5,395,233 A | 3/1995 | Karp | 431/289 |
| 5,432,204 A | 7/1995 | Farkas | 521/49 |
| 5,455,309 A | 10/1995 | Albini et al. | 525/420.5 |
| 5,455,326 A | 10/1995 | Parker | 528/335 |
| 5,500,209 A | 3/1996 | Ross et al. | 424/66 |
| 5,538,718 A | 7/1996 | Aul et al. | 424/64 |
| 5,578,089 A | 11/1996 | Elsamaloty | 44/275 |
| 5,585,057 A | 12/1996 | Trotta | 264/130 |
| 5,589,396 A | 12/1996 | Frye et al. | 436/73 |
| 5,597,300 A | 1/1997 | Wohl et al. | 431/288 |
| 5,603,925 A | 2/1997 | Ross et al. | 424/65 |
| 5,618,911 A | 4/1997 | Kimura et al. | 528/361 |
| 5,624,875 A | 4/1997 | Nakanishi et al. | 501/39 |
| 5,632,615 A | 5/1997 | DeGarmo | 431/288 |
| 5,645,632 A | 7/1997 | Palvin | 106/31.29 |
| 5,667,568 A | 9/1997 | Sacripante et al. | 106/20 R |
| 5,693,277 A | 12/1997 | Widmer | 264/153 |
| 5,783,657 A | 7/1998 | Pavlin et al. | 528/310 |
| 5,804,682 A | 9/1998 | Fischer et al. | 528/310 |
| 5,807,968 A | 9/1998 | Heinrich et al. | 528/310 |
| 5,852,118 A | 12/1998 | Horrion et al. | 525/90 |
| 5,902,841 A | 5/1999 | Jaeger et al. | 523/161 |
| D411,891 S | 7/1999 | Bell et al. | D26/6 |
| 5,932,630 A | 8/1999 | Kovacs et al. | 523/161 |
| 6,033,210 A | 3/2000 | Freeman | 431/291 |
| 6,068,472 A | 5/2000 | Freeman et al. | 431/291 |
| 6,111,055 A | 8/2000 | Berger et al. | 528/310 |
| 6,129,771 A | 10/2000 | Fike et al. | 44/275 |
| 6,214,063 B1 | 4/2001 | DeStefano et al. | 44/275 |
| 6,214,290 B1 | 4/2001 | Esposito | 422/1- |

ESTER-TERMINATED POLY(ESTER-AMIDES) USEFUL FOR FORMULATING TRANSPARENT GELS IN LOW POLARITY FLUIDS

TECHNICAL FIELD

The invention relates to gelling agents, and in particular to gellants for low polarity liquids such as hydrocarbons.

BACKGROUND OF THE INVENTION

Personal care products generally contain one or more active ingredients within a carrier formulation. While the active ingredient(s) determine the ultimate performance properties of the product, the carrier formulation is equally critical to the commercial success of the product. The rheology of the carrier (also referred to as the "base") largely determines the flow properties of the product, and the flow properties largely determine the manner in which the consumer will apply or use the product.

For example, aluminum chlorohydrate and aluminum-zirconium tetrachlorohydrex-Gly are metal salts that are commonly used as active ingredients in deodorant and antiperspirant products. Consumers have shown a preference for applying deodorant from a stick form. Thus, the carrier in a stick-form deodorant must be a relatively hard substance, and waxy fatty alcohol such as stearyl alcohol has been used as the carrier in these products. As another example, the active ingredient in a lipstick is the colorant. A lipstick should not be as hard as a stick deodorant, but of course must maintain its shape when undisturbed at room temperature. A blend of wax and oil is known to provide a consistency that is well-suited as a carrier for a lipstick. As a final example, shampoo desirably has a viscosity greater than water, and when the active ingredient(s) in a shampoo does not have a sufficiently high viscosity, a somewhat viscous carrier material is desirably included in the shampoo formulation.

From the above examples, it is seen that formulators of personal care products depend upon the availability of materials having various rheological properties, in order to formulate a successful personal care product. Materials which have a gel-like character, in that they maintain their shape when undisturbed but flow upon being rubbed, are often desired for personal care products.

Transparent (i.e., clear) carriers are needed by formulators who develop a personal care product wherein colorant is an active ingredient, because a transparent carrier (as opposed to an opaque carrier) will minimally, if at all, interfere with the appearance of the colorant. However, in recent years consumers have demonstrated an increasing preference for transparent personal care products such as deodorants and shampoos. There is thus an increasing demand for transparent materials which can provide the rheological properties needed for various personal care products, and particularly which can impart gel-like character to a formulation.

Polyamide resin prepared from polymerized fatty acid and diamine is reported to function as a gellant in formulations developed for personal care products. For example, U.S. Pat. No. 3,148,125 is directed to a clear lipstick composition formed from polyamide resin compounded with a lower aliphatic alcohol and a so-called "polyamide solvent." Likewise, U.S. Pat. No. 5,500,209 is directed to forming a gel or stick deodorant, where the composition contains polyamide gelling agent and a solvent system including monohydric or polyhydric alcohols. Thus, the prior art recognizes to blend certain polyamides with alcohols, to thereby form a gel.

Certain modified polyamide resins, e.g., polyamides which are only partly amidated but contain esterified carboxyl groups, have been reported to impart high gel strength and pronounced thixotropic properties to coating compositions that contain alkyd resins or drying oils. See U.S. Pat. No. 3,141,767 to Goetze et al. However, the modified polyamide resins of Goetze et al. are not disclosed as being useful gellants in personal care products, nor useful gellants when a low polarity fluid is used as the vehicle.

Low polarity fluids are desirably included in a personal care formulation because they are often transparent, relatively inexpensive, and non-toxic. Low polarity fluids are also available in a wide variety of viscosities and grades. However, low polarity fluids often do not have the rheological properties that are desired in a carrier, e.g., they do not naturally exhibit gel-like character. There is a need in the art for materials that can be combined with low polarity solvent, such as a hydrocarbon or fatty acid ester, to afford a transparent material which has gel-like character. The gel-like character is preferably of a smooth, silky feeling when the gel is rubbed against the skin. The present invention provides this and related advantages as described herein.

SUMMARY OF THE INVENTION

In one aspect, the present invention provides a resin composition prepared by reacting components comprising dibasic acid, diamine, polyol and monoalcohol, wherein
(a) at least 50 equivalent percent of the dibasic acid comprises polymerized fatty acid; and
(b) at least 50 equivalent percent of the diamine comprises ethylene diamine. Preferably,
(c) 10–60 equivalent percent of the total of the hydroxyl and amine equilvalents provided by diamine, polyol and monoalcohol are provided by monoalcohol; and
(d) no more than 50 equivalent percent of the total of the hydroxyl and amine equivalents provided by diamine, polyol and monoalcohol are provided by polyol.

In another aspect, the present invention provides a composition comprising (a) a resin composition prepared by reacting together components comprising dibasic acid, diamine, polyol and mono-alcohol, wherein at least 50 equivalent percent of the dibasic acid comprises polymerized fatty acid; and at least 50 equivalent percent of the diamine comprises ethylene diamine; and (b) hydrocarbon; the composition having a consistency of a gel. Preferably, 10–60 equivalent percent of the total of the hydroxyl and amine equilvalents provided by diamine, polyol and monoalcohol are provided by monoalcohol; and no more than 50 equivalent percent of the total of the hydroxyl and amine equivalents provided by diamine, polyol and monoalcohol are provided by polyol. In one aspect of the invention, some or all of the hydrocarbon is substituted with polydimethylsiloxanes (PDMS) or other silicon-containing material (such as phenylated silicones such as phenyl trimethicones, phenyl dimethicones and phenyl trimethylsiloxy diphenylsiloxanes etc.).

In another aspect, the present invention provides a composition comprising (a) a resin composition prepared by reacting together components comprising dibasic acid, diamine, polyol and mono-alcohol, wherein at least 50 equivalent percent of the dibasic acid is comprises polymerized fatty acid; and at least 50 equivalent percent of the diamine is ethylene diamine; and (b) an ester compound comprising the chemical group —O—C(=O)—, the composition having the consistency of a gel. Preferably, 10–60 equivalent percent of the total of the hydroxyl and amine equilvalents provided by diamine, polyol and monoalcohol are provided by monoalcohol; and no more than 50 equivalent percent of the total of the hydroxyl and amine equivalents provided by diamine, polyol and monoalcohol are provided by polyol.

In another aspect, the present invention provides a composition comprising (a) a resin composition prepared by reacting together components comprising dibasic acid, diamine, polyol and mono-alcohol, wherein at least 50 equivalent percent of the dibasic acid is comprises polymerized fatty acid; and at least 50 equivalent percent of the diamine is ethylene diamine; and (b) a polyester compound; the composition having a consistency of a gel. Preferably, 10–60 equivalent percent of the total of the hydroxyl and amine equilvalents provided by diamine, polyol and monoalcohol are provided by monoalcohol; and no more than 50 equivalent percent of the total of the hydroxyl and amine equivalents provided by diamine, polyol and monoalcohol are provided by polyol.

In another aspect, the present invention provides a method for preparing a resin composition comprising ester-terminated poly(ester-amide), the method comprising reacting w equivalents of hydroxyl from polyol or a reactive equivalent thereof, x equivalents of carboxylic acid from diacid or a reactive equivalent thereof, y equivalents of amine from diamine, and z equivalents of hydroxyl from monoalcohol or a reactive equivalent thereof under reactions conditions to provide a resin composition having an acid number of less than 20 and an amine number of less than 20, wherein at least about 50% of the carboxylic acid equivalents are from polymerized fatty acid, at least about 50% of the amine equivalents are from ethylene diamine, and monoalcohol is substantially the only monofunctional reactant used to form the resin. Preferably, 10–60 equivalent percent of the total of the hydroxyl and amine equilvalents provided by diamine, polyol and monoalcohol are provided by monoalcohol; and no more than 50 equivalent percent of the total of the hydroxyl and amine equivalents provided by diamine, polyol and monoalcohol are provided by polyol.

The present invention also provides a personal care product comprising a resin composition prepared by reacting components comprising dibasic acid, diamine, polyol and mono-alcohol, wherein (a) at least 50 equivalent percent of the dibasic acid comprises polymerized fatty acid; (b) at least 50 equivalent percent of the diamine comprises ethylene diamine; (c) 10–60 equivalent percent of the total of the hydroxyl and amine equilvalents provided by diamine, polyol and monoalcohol are provided by monoalcohol; and (d) no more than 50 equivalent percent of the total of the hydroxyl and amine equivalents provided by diamine, polyol and monoalcohol are provided by polyol.

In another aspect, the present invention provides a controlled release composition comprising a volatile component and a resin composition prepared by reacting components comprising dibasic acid, diamine, polyol and mono-alcohol, wherein (a) at least 50 equivalent percent of the dibasic acid comprises polymerized fatty acid; (b) at least 50 equivalent percent of the diamine comprises ethylene diamine; (c) 10–60 equivalent percent of the total of the hydroxyl and amine equilvalents provided by diamine, polyol and monoalcohol are provided by monoalcohol; and (d) no more than 50 equivalent percent of the total of the hydroxyl and amine equivalents provided by diamine, polyol and monoalcohol are provided by polyol.

In another aspect, the present invention provides a candle comprising a wick and a resin composition prepared by reacting components comprising dibasic acid, diamine, polyol and mono-alcohol, wherein (a) at least 50 equivalent percent of the dibasic acid comprises polymerized fatty acid; (b) at least 50 equivalent percent of the diamine comprises ethylene diamine; (c) 10–60 equivalent percent of the total of the hydroxyl and amine equilvalents provided by diamine, polyol and monoalcohol are provided by monoalcohol; and (d) no more than 50 equivalent percent of the total of the hydroxyl and amine equivalents provided by diamine, polyol and monoalcohol are provided by polyol; where the candle further comprises a solvent that is gelled by the resin.

These and other aspects of the present invention are described in further detail below.

DETAILED DESCRIPTION OF THE INVENTION

The present invention is directed to ester-terminated poly(ester-amides) (ETPEA) and a method of preparing a resinous composition (hereinafter, simply "a resin") comprising, in whole or part, EPTEA. A resin comprising ETPEA (an "ETPEA resin") is useful as a gelling agent for hydrocarbons and other low polarity liquids, where the resultant gels are useful components in, for example, personal care products, candles, lubricants, inks, corrosion inhibitors, cosmetic formulations and other products that can benefit from gel-like character.

In one aspect, the present invention provides a resin composition prepared by reacting components comprising dibasic acid, diamine, polyol and mono-alcohol, wherein at least 50 equivalent percent of the dibasic acid comprises polymerized fatty acid; and at least 50 equivalent percent of the diamine comprises ethylene diamine. Before further describing this resin, and other aspects of the present invention, the reactants useful in preparing the resin will be described.

The dibasic acid is an organic molecule containing two carboxylic acid groups or reactive equivalents thereof. A preferred dibasic acid is polymerized fatty acid, and in particular the dimer acid component of polymerized fatty acid. Polymerized fatty acid is typically a mixture of structures, including dimer acid and trimer acid, where individual dimer acids may be saturated, unsaturated, cyclic, acyclic, etc. Polymerized fatty acid as used to form the resin of the invention is a well known material of commerce, and thus need not be described in great detail. Polymerized fatty acid is typically formed by heating long-chain unsaturated fatty acids, e.g., $C_{18}$ monocarboxylic acids, to about 200–250° C. in the presence of a clay catalyst in order that the fatty acids polymerize. The product typically comprises dimer acid, i.e., $C_{36}$ dicarboxylic acid formed by dimerization of the fatty acid, and trimer acid, i.e., $C_{54}$ tricarboxylic acid formed by trimerization of the fatty acid. A more detailed discussion of fatty acid polymerization may be found in, e.g., U.S. Pat. No. 3,157,681 and *Naval Stores—Production, Chemistry and Utilization*, D. F. Zinkel and J. Russell (eds.), Pulp. Chem. Assoc. Inc., 1989, Chapter 23.

Because fatty acid polymerization typically forms much more dimer acid than trimer acid, those skilled in the art may often refer to polymerized fatty acid as dimer acid, even though some trimer acid, and even higher polymerization products, may be present with the dimer acid. It is preferred that the polymerized fatty acid contain less than about 20 weight percent of trimer acid, based on the total weight of the polymerized fatty acid, and that the dimer acid constitute at least about 80 weight percent of the polymerized fatty acid. More preferably, the dimer acid constitutes essentially all of the polymerized fatty acid.

Typical unsaturated fatty acids used to form polymerized fatty acid include oleic acid, linoleic acid, linolenic acid, etc. Tall oil fatty acid, which is a mixture containing long-chain unsaturated fatty acids obtained as a byproduct of the wood pulping process, is preferred for preparing polymerized fatty acid useful in the invention. While tall oil fatty acid is a preferred source of long-chain fatty acid, the polymerized fatty acid may alternatively be prepared by polymerization of unsaturated fatty acids from other sources, e.g., soybeans or canola. The polymerized fatty acid useful in the invention is a liquid, with an acid number on the order of about 180 to about 200.

The polymerized fatty acid of the invention may be hydrogenated prior to being used in the resin-forming reaction of the invention. Hydrogenation tends to provide for a slightly higher melting point for the inventive resin, as well as provide the resin with greater oxidative and color stability. Hydrogenated polymerized fatty acid tends to provide for a lighter colored resin, and is a preferred polymerized fatty acid for use in the practice of the present invention.

Polymerized fatty acid, dimer acid, and hydrogenated versions thereof may be obtained from a number of commercial suppliers. For example, Arizona Chemical (Jacksonville, Fla.) sells polymerized fatty acid under their UNIDYME® trademark.

In addition to polymerized fatty acid, or reactive equivalents thereof, the dibasic acid may comprise dibasic acid of the formula HOOC—$R^1$—COOH or reactive equivalents thereof, which may be referred to herein as co-diacid. In one aspect, $R^1$ contains 4 to 19, preferably about 4 to 12, and more preferably about 4 to 8 carbon atoms. The carbon atoms may be arranged in a linear, branched or cyclic fashion, and unsaturation may be present between any two carbon atoms. Thus, $R^1$ may be aliphatic or aromatic. When present, these lower carbon-number $R^1$ groups are preferably formed entirely of carbon and hydrogen, i.e., are hydrocarbon groups.

An exemplary co-diacid is a so-called "linear" diacid of the formula HOOC—$R^1$—COOH wherein $R^1$ is a linear $C_{4-12}$ hydrocarbon group, and more preferably is a linear $C_{6-8}$ hydrocarbon group. Linear co-diacids suitable for the present invention include 1,6-hexanedioic acid (adipic acid), 1,7-heptanedioic acid (pimelic acid), 1,8-octanedioic acid (suberic acid), 1,9-nonanedioic acid (azelaic acid), 1,10-decanedioic acid (sebacic acid), 1,11-undecanedoic acid, 1,12-dodecanedioic acid (1,10-decanedicarboxylic acid), 1,13-tridecanedioic acid (brassylic acid) and 1,14-tetradecanedioic acid (1,12-dodecanedicarboxylic acid).

Another exemplary co-diacid for use in the present invention is the reaction product of acrylic or methacrylic acid (or the ester thereof, with a subsequent hydrolysis step to form an acid) and an unsaturated fatty acid. For example, a $C_{21}$ diacid of this type may be formed by reacting acrylic acid with a $C_8$ unsaturated fatty acid (e.g., oleic acid), where an ene-reaction presumably occurs between the reactants. An exemplary $C_{21}$ diacid is commercially available from Westvaco Corporation, Chemical Division, Charleston Heights, S.C., as their product number 1550.

Aromatic diacids may be used as the co-diacid. An "aromatic diacid" as used herein is a molecule having two carboxylic acid groups (—COOH) or reactive equivalents thereof (e.g., acid chloride (—COCl) or ester (—COOR)) and at least one aromatic ring ("Ar"). Phthalic acids, e.g., isophthalic acid and terephthalic acid, are exemplary aromatic diacids. The aromatic diacid may contain aliphatic carbons bonded to the aromatic ring(s), as in HOOC—$CH_2$—Ar—$CH_2$—COOH and the like. The aromatic diacid may contain two aromatic rings, which may be joined together through one or more carbon bonds, (e.g., biphenyl with carboxylic acid substitution) or which may be fused (e.g., naphthalene with carboxylic acid substitution).

In one aspect, the resin is prepared with co-diacid and the co-diacid is selected from 1,4-cyclohexane dicarboxylic acid, isophthalic acid, adipic acid, azeleic acid, sebacic acid, and dodecandioic acid.

The diamine reactant has two amine groups, both of which are preferably primary amines, and is represented by the formula HN($R^{2a}$)—$R^2$—N($R^{2a}$)H. $R^{2a}$ is preferably hydrogen, but may also be an alkyl group or may also join together with $R^2$ or another $R^{2a}$ to form a heterocyclic structure. A preferred diamine is ethylene diamine, i.e., a diamine wherein $R^{2a}$ is hydrogen and $R^2$ is —$CH_2CH_2$—.

Diamines other than ethylene diamine may be referred to herein as co-diamines. When present, co-diamines are preferably used in a minor amount compared to the ethylene diamine. In a co-diamine, $R^2$ may be a hydrocarbon group having at least three carbon atoms, where the carbon atoms may be arranged in a linear, branched or cyclic fashion, and the group may be saturated or contain unsaturation. Thus, $R^2$ may be aliphatic or aromatic. Preferred $R^2$ hydrocarbon groups in the co-diamine have 2 to 36 carbon atoms, more preferred $R^2$ hydrocarbon groups have 2 to 12 carbon atoms, and still more preferred hydrocarbon groups have 2 to 6 carbon atoms.

Exemplary co-diamines having hydrocarbon $R^2$ groups include, without limitation, 1,2-diaminopropane, 1,3-diaminopropane, 1,4-diaminobutane, 1,2-diamino-2-methylpropane, 1,3-diaminopentane, 1,5-diaminopentane, 2,2-dimethyl-1,3-propanediamine, 1,6-hexanediamine (also known as hexamethylenediamine, HMDA), 2-methyl-1,5-pentanediamine, 1,7-diaminoheptane, 1,8-diaminooctane, 2,5-dimethyl-2,5-hexanediamine, 1,9-diaminononane, 1,10-diaminodecane, 1,12-diaminododecane, diaminophenanthrene (all isomers, including 9,10), 4,4'-methylenebis (cyclohexylamine), 2,7-diaminofluorene, phenylene diamine (1,2; 1,3 and/or 1,4 isomers), adamantane diamine, 2,4,6-trimethyl-1,3-phenylenediamine, 1,3-cyclohexanebis (methylamine), 1,8-diamino-p-menthane, 2,3,5,6-tetramethyl-1,4-phenylenediamine, diaminonaphthalene (all isomers, including 1,5; 1,8; and 2,3) and 4-amino-2,2,6,6-tetramethylpiperidine.

Suitable aromatic co-diamines (by which is meant molecules having two reactive, preferably primary amine groups (—$NH_2$) and at least one aromatic ring ("Ar") include xylene diamine and naphthalene diamine (all isomers).

The $R^2$ group of the co-diamine may contain oxygen atoms in the form of a polyalkylene oxide group. Exemplary polyalkylene oxide-based co-diamines include, without limitation, the JEFFAMINE™ diamines, i.e., poly (alkyleneoxy)diamines from Huntsman Chemical (Salt Lake City, Utah), also known as polyether diamines. Preferred polyalkylene oxide-containing co-diamines are the JEFFAMINE® ED, XTJ and D series diamines. Ether-containing $R^2$ groups are not preferred, as they tend to lower the melting point of the resin to an undesirable extent. However, small amounts of a polyalkylene oxide-based co-diamine with a major amount of ethylene diamine are suitable for use in the invention.

The $R_2$ group of the co-diamine may contain nitrogen atoms, where these nitrogen atoms are preferably secondary or tertiary nitrogen atoms. A typical nitrogen atom-containing $R^2$ group having secondary nitrogen atoms is a polyalkylene amine, i.e., a group containing alternating alkylene groups and amine groups (i.e., —NH— groups). The alkylene group is preferably ethylene, i.e., —CH$_2$CH$_2$—, and the polyalkylene amine may be represented by the formula NH$_2$—(CH$_2$CH$_2$NH)$_m$CH$_2$CH$_2$—NH$_2$ wherein m is an integer from 1 to about 5. Diethylenetriamine (DETA) and triethylenetetraamine (TETA) are representative examples. When the diamine contains two primary amines in addition to secondary amines, the EPTEA-forming reaction is preferably conducted at relatively low temperature, so that the primary amines (in preference to the secondary amines) react with the diacid component.

However, the nitrogen atoms in the nitrogen-containing $R^2$ group may also be present as tertiary nitrogen atoms, e.g., they may be present in a heterocycle of the formula:

wherein $R_c$ is a $C_{1-3}$ alkyl group. Bis(aminoethyl)-N,N'-piperazine and bis(aminopropyl)-N,N'-piperazine may be used to introduce these $R^2$ groups into an ETPEA molecule, and these are such co-diamines according to the invention. In addition, the co-diamine may have one primary amine group and one secondary amine group (e.g., N-ethylethylenediamine or 1-(2-aminoethyl)piperazine). Generally, it is preferred that amine compounds having secondary amines not be present in the reaction mixture to any great extent, because their incorporation into an ester terminated polyamide tends to provide for poorer gelling ability of the ester-terminated polyamide.

In general, the diamine reactant may have the formula HN($R^{2a}$)—$R^2$—NH($R^{2a}$) wherein $R^{2a}$ is preferably hydrogen, but may also be $C_{1-10}$alkyl, preferably $C_{1-5}$alkyl, and more preferably $C_{1-3}$alkyl. In addition, $R^{2a}$ may join together with $R^2$ or another $R^{2a}$ group to form a heterocyclic structure. For example, when piperazine is used as a co-diamine, the two $R^{2a}$ groups in the HN($R^{2a}$)—$R^2$—NH($R^{2a}$) structure have joined together to form an ethylene bridge.

In one aspect, the ETPEA resin of the invention is prepared from co-diamine, where the co-diamine is selected from 1,6-hexanediamine, xylenediamine, 1,2-propanediamine, 2-methylpentamethylenediamine, and 1,12-dodecanediamine. Suitable diamines of the present invention are available from a number of commercial sources including Aldrich (Milwaukee, Wis.; http://www.aldrich.sial.com); EM Industries, Inc. (Hawthorne, N.Y.; http://www.emscience.com); Lancaster Synthesis, Inc. (Windham, N.H.; http://www.lancaster.co.uk); Spectrum Quality Product, Inc. (New Brunswick, N.J.; http://www.spectrumchemical.com).

The monoalcohol may be represented by the formula $R^3$—OH, wherein $R^3$ is preferably a hydrocarbon group having at least ten carbon atoms. Thus, the monoalcohol can also be described as a monohydric alcohol. In one aspect, $R^3$ is a $C_{10-30}$ hydrocarbon, preferably a $C_{12-24}$ hydrocarbon, still more preferably is a $C_{16-22}$ hydrocarbon, and yet still more preferably is a $C_{18}$ hydrocarbon. As used herein, the term $C_{10-30}$ hydrocarbon refers to a hydrocarbon group having at least 10, but not more than 30 carbon atoms, and similar terms have an analogous meaning. The carbon atoms of the hydrocarbon group may be arranged in a linear, branched or cyclic fashion, and the group may be saturated or unsaturated. However, in one aspect of the present invention, $R^3$ is linear, with the hydroxyl group located on a terminal carbon atom, i.e., the monoalcohol is a primary monoalcohol. Thus, 1-dodecanol, 1-tetradecanol, 1-hexadecanol (cetyl alcohol), 1-octadecanol (stearyl alcohol), 1-eicosanol (arachidyl alcohol) and 1-docosanol (behenyl alcohol) are preferred monoalcohols for preparing resins of the invention, where names in parentheses are common or trivial names by which these monoalcohols are known. While the monoalcohol has been exemplified with saturated alkyl groups, the monoalcohol may alternatively contain an alkenyl group, i.e., an alkyl group having unsaturation between at least any two adjacent carbon atoms. One or a mixture of these alcohols may be used to prepare a resin of the invention.

Another monoalcohol reactant suited for the invention is a so-called Guerbet alcohol. Guerbet alcohols have the general formula H—C(Ra)(Rb)—CH$_2$—OH wherein Ra and Rb may be the same or different and preferably represent a $C_{6-12}$ hydrocarbon group. Further discussion of Guerbet alcohols may be found in, e.g., "Dictionary For Auxiliaries For Pharmacy, Cosmetics And Related Fields," H. P. Fiedler, 3$^{rd}$ Ed., 1989, Cantor Aulendorf. 2-Hexadecyloctadecanol, which has 24 carbon atoms, is a preferred Guerbet alcohol for use in the present invention.

Another suitable monoalcohol reactant is a linear wax alcohol. Suitable linear wax alcohols are commercially available from, e.g., Petrolite Corporation (Tulsa, Okla.) under their UNILIN® trademark. These wax alcohols are typically a blend of linear alcohols having at least about 20 carbon atoms, and more typically at least about 24 carbon atoms. Vapor pressure osmometry (VPO), among many other techniques, may be used to characterize the number average molecular weight of a blend of alcohols. In one aspect, the mixture of monohydric linear wax alcohols has a number average molecular weights by VPO of about 200 to about 800, preferably about 300 to about 600. Pure $C_{22}$ monohydric linear alcohol has a molecular weight of 326 by VPO.

The monohydric alcohol, whether present as an essentially pure alcohol or in a mixture of monohydric alcohols, preferably has a straight chain alkyl group. Exemplary alcohols useful in the invention include 1-eicosanol ($C_{20}$), 1-docosanol ($C_{22}$, also known as behenyl alcohol), dotriacontanol ($C_{32}$), tetratriacontanol ($C_{34}$), pentatriacontanol ($C_{35}$), tetracontanol ($C_{40}$), tetraacontanol ($C_{44}$), dopentaacontanol ($C_{54}$), tetrahexaacontanol ($C_{64}$), dohexaacontanol ($C_{72}$), etc.

A final ingredient necessary in preparing an ETPEA resin of the present invention is polyol, which may also be referred to as polyhydric alcohol. The polyol is of the formula $R^4$(OH)$_n$ wherein $R^4$ is an n-valent organic group. For instance, $R^4$ may be a $C_2$-$C_{20}$ organic group without hydroxyl substitution. As another example, $R^4$ may be a hydrocarbon. Typically, n is selected from 2, 3, 4, 5 and 6. Suitable polyols for use in preparing an ETPEA resin of the present invention include ethylene glycol, propylene glycol, butylene glycol, glycerol, trimethylolpropane, pentaerythritol, neopentyl glycol, tris(hydroxymethyl)methanol, di-pentaerythritol, and tri-pentaerthyritol.

Reactive equivalents of diacids and/or diamines may be used in the invention. For example, diesters may be substituted for some or all of the diacid, where "diesters" refer to the esterification product of diacid with hydroxyl-containing molecules. However, such diesters are preferably prepared from relatively volatile hydroxyl-containing molecules, in order that the hydroxyl-containing molecule may be easily removed from the reaction vessel subsequent to monoalcohol and/or diamine (both as defined herein) reacting with the diester. A lower alkyl diester, e.g., the esterification or diesterification product of diacid as defined herein and a $C_{1-4}$ monohydic alcohol (e.g., methanol, ethanol, propanol and butanol), may be used in place of some or all of the diacid in the ETPEA-resin forming reaction of the invention. The acid halide of the diacid may likewise be employed in place of some or all of the diacid, however such a material is typically much more expensive and difficult to handle compared to the diacid, and thus the diacid is preferred. Likewise, the monoalcohol may be esterified with a volatile acid, e.g., acetic acid, prior to being employed in the ETPEA resin-forming reaction of the invention. While such reactive equivalents may be employed in the reaction, their presence is not preferred because such equivalents introduce undesired reactive groups into the reaction vessel.

In preparing a resin of the invention, the above-described reactants may be combined in any order. Preferably, the reactants are simply mixed together and heated for a time and at a temperature sufficient to achieve essentially complete reaction, to thereby form the inventive resin. The terms "complete reaction" and "reaction equilibrium" as used herein have essentially the same meaning, namely that further heating of the product resin does not result in any appreciable change in the performance characteristics of the product resin, where the most relevant performance characteristic is the ability of the product resin to form a clear, firm gel upon being combined with a solvent (as mentioned above and discussed further below).

Thus, the ETPEA resin may be formed in a one-step procedure, wherein all of the dibasic acid, diamine, polyol and monoalcohol (including co-diacid and co-diamine, if present) are combined and then heated to about 200–250° C. for a few hours, typically 2–8 hours. As one or more of the reactants may be a solid at room temperature, it may be convenient to combine each of the ingredients at a slightly elevated temperature, and then form a homogeneous mixture prior to heating the reaction mixture to a temperature sufficient to cause reaction between the dibasic acid, diamine, polyol and monoalcohol. Alternatively, although less preferably, two or three of the reactants may be combined and reacted together, and then the remaining reactant(s) is/are added followed by further heating the desired product is obtained. Reaction progress may be conveniently monitored by periodically measuring the acid and/or amine number of the product mixture.

Any catalyst that may accelerate amide formation between carboxylic acid and amine groups, and/or ester formation between carboxylic acid and hydroxyl groups, may be present in the reaction mixture described above. Thus, mineral acid such as phosphoric acid, or tin salts such as dibutyltin oxide, may be present during the reaction. In addition, it is preferred to remove water from the reaction mixture as it is formed upon amide and ester formation. This is preferably accomplished by maintaining a vacuum on he reacting mixture.

It is important to control the stoichiometry of the reactants in order to prepare ester-terminated poly(ester-amides) according to the invention. In the following discussion regarding reactant stoichiometry, the terms "equivalent(s)" and "equivalent percent" will be used, and are intended to have their standard meanings as employed in the art. However, for additional clarity, it is noted that equivalents refer to the number of reactive groups present in a molar quantity of a molecule, such that a mole of a dibasic acid (e.g., sebacic acid) has two equivalents of carboxylic acid, while a mole of monoalcohol has one equivalent of hydroxyl. Furthermore, it is emphasized that the dibasic acid has only two reactive groups (both carboxylic acids), the monoalcohol has only one reactive group (a hydroxyl group), the diamine has only two reactive groups (preferably both primary amines), and the polyol has at least two reactive groups (i.e., at least two reactive hydroxyl groups) and these are preferably, although not necessarily, the only reactive materials present in the reaction mixture.

According to the invention, is it preferred that the equivalents of carboxylic acid are substantially equal to the combined equivalents of hydroxyl contributed by monoalcohol and polyol, and amine contributed by diamine. In other words, if the reaction mixture used to form an ETPEA resin has "x" equivalents of carboxylic acid, "y" equivalents of amine and "z" equivalents of hydroxyl (from the combination of monoalcohol and polyol), then $0.9 \leq \{x/(y+z)\} \leq 1.1$, and preferably $\{x/(y+z)\}$ is substantially 1.0. Under these conditions, substantially all of the carboxylic acid groups will react with substantially all of the hydroxyl and amine groups, so that the final product contains very little unreacted carboxylic acid, hydroxyl or amine groups. In other words, each of the acid and amine numbers of a resin of the invention is preferably less than about 25, is more preferably less than about 15, and is more preferably less than about 10, and is still more preferably less than about 5.

When co-diacid is employed to prepare an ETPEA resin, the co-diacid preferably contributes no more than about 50% of the equivalents of carboxylic acid present in the reaction mixture. Stated another way, the co-diacid contributes from 0–50 equivalent percent of the acid equivalents in the reaction mixture. Preferably, the co-diacid contributes 0–25 equivalent percent, and more preferably contributes 0–10 equivalent percent of the acid equivalents in the reaction mixture.

When co-diamine is employed to prepare an ETPEA resin, the co-diamine present in the reaction mixture preferably contributes no more than about 50% of the equivalents of amine present in the reaction mixture Stated another way, the co-diamine contributes from 0–50 equivalent percent of the amine equivalents in the reaction mixture. Preferably, the co-diamine contributes 0–25 equivalent percent, and more preferably contributes 0–10 equivalent percent of the amine equivalents in the reaction mixture.

The stoichiometry of the reactants will have a significant impact on the composition and properties of the ETPEA resin. For example, ETPEA resins made with increasing amounts of monoalcohol will tend to have lower average molecular weights. In other words, as more monofunctional reactant is used, the number of amide pairs in an average ETPEA molecule of the resin will tend to decrease. On the other hand, as less monoalcohol is used, the average molecular weight of the ETPEA in the resulting resin will increase. In general, increasing the average molecular weight for the ETPEAs in a resin will tend to increase the melting point and melt viscosity of the resin, which tends to provide a firmer gel when the ETPEA resin is combined with a low polarity liquid. However, when the average molecular weight of the ETPEA increases to a certain point, the EPTEA resins become insoluble in low polarity solvents, and therefore do not form desirable gels. Therefore, in a preferred aspect of the invention, the monoalcohol level in the reactants should be such that at least 10 equivalent percent of the total amine and hydroxyl equivalents should be derived from monoalcohol.

The amount of polyol used in the reactant formulation will also have an impact on the properties of the ETPEA resin. Increasing the level of polyol relative to the other reactants tends to decrease the softening point of the ETPEA resin. When the polyol contributes greater than about 50 equivalent percent of the total equivalents of hydroxyl and amine groups present in the ETPEA-forming reaction mixture, then the resulting ETPEA resin becomes undesirably "soft" and mixtures of this soft resin with a low polarity fluid tends to form more of a viscous oil than a gel. Accordingly, in one aspect of the invention, the hydroxyl equivalents from polyol are less than or equal to 50% of the total hydroxyl and amine equivalents contributed by the total of the polyol, monoalcohol and diamine reactants. In other aspects, the hydroxyl equivalents from polyol are less than or equal to 40%, or 30% or 20%, of the total hydroxyl and amine equivalents contributed by the total of the polyol, monoalcohol and diamine reactants.

In one aspect of the invention, the amine equivalents from diamine equals 0.3 to 0.75 of the total amine and hydroxyl equivalents provided by diamine, polyol and mono-alcohol. In another aspect, the hydroxyl equivalents from polyol equals 0.05 to 0.45 of the total amine and hydroxyl equivalents provided by diamine, polyol and mono-alcohol. In another aspect, the hydroxyl equivalents from mono-alcohol equals 0.20 to 0.45 of the total amine and hydroxyl equivalents provided by diamine, polyol and mono-alcohol.

For example, in one aspect the invention provides a resin prepared as described herein where the amine equivalents from diamine equals 0.30 to 0.75 of the total amine and hydroxyl equivalents provided by diamine, polyol and mono-alcohol; the hydroxyl equivalents from polyol equals 0.05 to 0.45 of the total amine and hydroxyl equivalents provided by diamine, polyol and mono-alcohol; and the hydroxyl equivalents from mono-alcohol equals 0.20 to 0.45 of the total amine and hydroxyl equivalents provided by diamine, polyol and monoalcohol. As another example, the present invention provides a resin prepared by reacting dibasic acid, diamine, polyol and monoalcohol where polymerized fatty acid constitutes at least 60 equivalent percent of the acid equivalents of the dibasic acid, ethylene diamine constitutes at least 75 equivalent percent of the amine equivalents of the amine; the amine equivalents from diamine equals 0.30 to 0.75 of the total amine and hydroxyl equivalents provided by diamine, polyol and mono-alcohol; the hydroxyl equivalents from polyol equals 0.05 to 0.45 of the total amine and hydroxyl equivalents provided by diamine, polyol and mono-alcohol; and the hydroxyl equivalents from mono-alcohol equals 0.20 to 0.45 of the total amine and hydroxyl equivalents provided by diamine, polyol and mono-alcohol.

In one aspect, the present invention provides a method for preparing a resin composition comprising ester-terminated poly(ester-amide), the method comprising reacting w equivalents of hydroxyl from polyol or a reactive equivalent thereof, x equivalents of carboxylic acid from diacid or a reactive equivalent thereof, y equivalents of amine from diamine, and z equivalents of hydroxyl from monoalcohol or a reactive equivalent thereof under reactions conditions to provide a resin composition having an acid number of less than 20 and an amine number of less than 20, wherein at least about 60% of the carboxylic acid equivalents are from polymerized fatty acid, at least about 60% of the amine equivalents are from ethylene diamine, and mono-alcohol is substantially the only monofunctional reactant used to form the resin. In a preferred embodiment, $w/(w+y+z)$ is within the range of about 0.05 to 0.60; $y/(w+y+z)$ is within the range of about 0.20 to 0.75; and $z/(w+y+z)$ is within the range of 0.20 to 0.50.

As stated above, the ester-terminated poly(ester-amides) described herein are useful in forming gels with solvents at room temperature, and accordingly preferably have a softening point greater than room temperature. A precise definition of "gel" is not easy to give, although most if not all researchers recognize a "gel." Generally, a gel is more viscous than a liquid or paste, and retains its shape when left undisturbed, i.e., is self-supporting. However, a gel is not as hard or firm as a stick or wax. Gels may be penetrated more easily than a wax-like solid, where "hard" gels are relatively more resistant to penetration than "soft" gels.

Almdale et al. (*Polymer Gels and Networks*, Vol. 1, No. 5 (1993)) list two criteria for defining a system as a gel: (1) a gel consists of two or more components, one of which is a liquid, present in substantial quantities; and (2) a gel is a soft material which is solid or solid-like. This latter requirement can be described more accurately through rheological measurement. Typically, gels possess a storage modulus $G'(w)$ which exhibits a pronounced plateau at higher frequencies (on the order of 1–100 radians/second), and a loss modulus $G''(w)$ which is considerably smaller than the storage modulus in the plateau region. In a strict sense, the term "gel" applies to systems having a value $G'(w)$ that is higher than its value of $G''(w)$ at low frequencies. Many of the compositions according to the present invention are gels by one or both of the above definitions. A gel is free-standing standing or self-supporting in that its yield value is greater than the sheer stress imposed by gravity.

A commercially desirable aspect of the invention is that the gel may be (although need not be) essentially transparent. Thus, the gels are desirably combined with colorants, as well as other ingredients, to form lipstick and other cosmetic products. The advantage of a clear gel in these applications is that the gel imparts little if any undesirable color to the lipstick or cosmetic. The gels may be combined with aluminum zirconium salts, as well as other ingredients, to form colorless underarm deodorant/antiperspirant, which is currently quite popular. The gels of the invention are also useful in other personal care products, e.g., cosmetics such as eye make-up, lipstick, foundation make-up, costume make-up, as well as baby oil, make-up removers, bath oil, skin moisturizers, sun care products, lip balm, waterless hand cleaner, medicated ointments, ethnic hair care products, perfume, cologne, and suppositories. In addition, the gels may be used in household products such as automobile wax/polish, candles, furniture polish, metal cleaners/polishes, household cleaners, paint strippers and insecticide carriers.

The gels may also be used in industrial products such as fuels (sterno, lighters), toilet bowl rings, lubricants/greases, wire rope lubricant, joint and cable fillers, soldering flux, buffing compounds, crayons and markers, modeling clay, rust preventatives, printing inks, protective/removable coatings, and jet inks. For example, a hydrocarbon oil gelled with an ETPEA resin of the invention may be used as a heat source in, e.g., a cooking apparatus used in camping and hiking. Such a composition will not flow if tilted, and thus may be safer and neater than similar products made from flowing materials.

Formulations to prepare such materials are well known in the art. For example, U.S. Pat. Nos. 3,615,289, 3,645,705, 6,111,055, 6,129,771 and 6,214,063 describe the formulation of candles and pigmented objects embedded in candles referred in the art as "icons." U.S. Pat. Nos. 3,148,125 and 5,538,718 describe the formulation of lipstick and other cosmetic sticks. U.S. Pat. Nos. 4,275,054, 4,937,069, 5,069, 897, 5,102,656 and 5,500,209 each describe the formulation of deodorant and/or antiperspirant. Each of these U.S. Patents is hereby incorporated fully herein by reference.

The ETPEA resin of the invention may be incorporated into commercial products such as those listed above by blending the ETPEA resin with the other components of the product. Typically, the ETPEA resin will be present at a concentration of about 1% to about 50% of the composition, based on the total weight of the composition. It is a routine matter to optimize the amount of ETPEA resin to have present in a composition, and indeed the amount will vary depending on the actual product and the desired consistency of the product. In general, as more ETPEA resin is used in a formulation, the product will display a more pronounced gel character.

Accordingly, another aspect of the invention is a gel formed between ingredients comprising ester-terminated poly(ester-amide) as described above and a non-aqueous liquid, preferably a low-polarity liquid. A preferred low polarity liquid is a hydrocarbon, with preferred hydrocarbons being solvents and oils. Solvents and oils may be distinguished in that defatting occurs when solvents are rubbed on human skin, leading to drying and irritation. However, defatting does not occur when oils are rubbed on human skin. Oils are more preferred than solvents in most personal-care formulations, and thus are preferred in forming the gels of the present invention. Preferably, the hydrocarbon has a relatively high number of carbon atoms, e.g., 10 to 30 carbon atoms, and thus is not a volatile hydrocarbon.

A preferred oil is mineral oil, also sometimes referred to as medicinal oil. Mineral oil is a highly refined, colorless, tasteless, and odorless petroleum oil (i.e., derived by processing petroleum/crude oil) used medicinally as an internal lubricant and for the manufacture of salves and ointments. Such mineral oils are highly refined in having substantially all volatile hydrocarbons removed therefrom, and in being hydrogenated (also called hydrotreated) in order to remove substantially all unsaturation, e.g., aromatic groups have been reduced to the fully saturated analog. A preferred mineral oil to prepare a gel of the invention is so-called "white" mineral oil, which is water-white (i.e., colorless and transparent) and is generally recognized as safe for contact with human skin. Mineral oil may also be characterized in terms of its viscosity, where light mineral oil is relatively less viscous than heavy mineral oil, and these terms are defined more specifically in the U.S. Pharmacopoeia, $22^{nd}$ revision, p. 899 (1990). Any mineral oil may be used in the invention to form a gel.

Other hydrocarbons that may be used in the invention include relatively lower molecular weight hydrocarbons including linear saturated hydrocarbons such a tetradecane, hexadecane, octadecane, etc. Cyclic hydrocarbons such as decahydronaphthalene (DECALIN), fuel grade hydrocarbons, branched chain hydrocarbons such as PERMETHYL from Permethyl Corporation and ISOPAR from Exxon Corp., and hydrocarbon mixtures such as product PD-23 from Witco (Greenwich, CT) may also be used in preparing gels of the invention. Such hydrocarbons, particularly saturated hydrocarbon oils, are a preferred liquid for preparing a gel of the invention because such hydrocarbons are often less irritating to the skin than liquids containing aromatic, ketone and other functional groups.

Another class of suitable low polarity liquids are esters, and particularly esters of fatty acids. Such esters may be monofunctional esters (i.e., have a single ester moiety) or may be polyfunctional (i.e., have more than one ester group). Suitable esters include, but are not limited to, the reaction products of $C_{1-24}$ monoalcohols with $C_{1-22}$ monocarboxylic acids, where the carbon atoms may be arranged in a linear, branched and/or cyclic fashion, and unsaturation may optionally be present between carbon atoms. Preferably, the ester has at least about 18 carbon atoms. Examples include, but are not limited to, fatty acid esters such as isopropyl isostearate, n-propyl myristate, isopropyl myristate, n-propyl palmitate, isopropyl palmitate, hexacosanyl palmitate, octacosanyl palmitate, triacontanyl palmitate, dotriacontanyl palmitate, tetratriacontanyl palmitate, hexacosanyl stearate, octacosanyl stearate, triacontanyl stearate, dotriacontanyl stearate and tetratriacontanyl stearate; salicylates, e.g., $C_{1-10}$ salicylates such as octyl salicylate, and benzoate esters including $C_{12-15}$ alkyl benzoate, isostearyl benzoate and benzyl benzoate.

Suitable esters are those commonly employed in the cosmetics industry for the formulation of lipstick and make-up, e.g., the fatty acid esters mentioned above, and are often denoted as "cosmetic esters." Other cosmetic esters include glycerol and propylene glycol esters of fatty acids, including the so-called polyglycerol fatty acid esters and triglycerides. Exemplary cosmetic esters include, without limitation, propylene glycol monolaurate, polyethylene glycol (400) monolaurate, castor oil, triglyceryl diisostearate and lauryl lactate. Thus, the liquid may have more than one of ester, hydroxyl and ether functionality. For example, $C_{10-15}$ alkyl lactate may be used in a gel of the invention. In addition, esterified polyols such as the polymers and/or copolymers of ethylene oxide, propylene oxide and butylene oxide reacted with $C_{1-22}$ monocarboxylic acids are useful. The carbon atoms of the $C_{1-22}$ monocarboxylic acids may be arranged in a linear, branched and/or cyclic fashion, and unsaturation may be present between the carbon atoms. Preferred esters are the reaction product of an alcohol and a fatty acid, where the alcohol is selected from $C_{1-10}$ monohydric alcohol, $C_{2-10}$ dihydric alcohol and $C_{3-10}$ trihydric alcohol, and the fatty acid is selected from a $C_{8-24}$ fatty acid.

The gels of the invention preferably do not contain substantial amounts of unreacted monoalcohol, i.e., monohydric alcohols having a single hydroxyl and their only functional group. Thus, the gels of the invention preferably contain less than 25 weight percent, more preferably less than 10 weight percent, and still more preferably less than 5 weight percent of unreacted monoalcohol.

The gels of the invention are preferably self-supporting, in that they retain their shape at room temperature and in the absence of shear. Also, the inventive gels are preferably clear or translucent. The terms clear, transparent and clarity are intended to have their ordinary dictionary definitions; thus, a clear gel allows ready viewing of objects behind it. By contrast, a translucent gel, although allowing light to pass through, causes the light to be so scattered that it will be impossible to see clearly objects behind the translucent stick. As used herein, a gel is transparent or clear if the maximum transmittance of light of any wavelength in the range 400 to 800 nm through a sample 1 cm thick is at least 35%, preferably at least 50% (see, e.g., European Patent Publication No. 291,334 A4). The gel is translucent if the maximum transmittance of such light through the sample is between 2% and less than 35%. The transmittance can be measured by placing a sample of the aforementioned thickness into a light beam of a spectrophotometer whose working range includes the visible spectrum, such as a Bausch & Lomb Spectronic 88 Spectrophotometer.

The gels of the invention preferably do not display syneresis. As defined in the McGraw-Hill Dictionary of Scientific and Technical Terms ($3^{rd}$ Edition), syneresis is the spontaneous separation of a liquid from a gel or colloidal suspension due to contraction of the gel. Typically, syneresis is observed as the separation of liquid from a gel, and is sometimes referred to as "bleeding," in that wetness is seen along the surfaces of a gel that displays syneresis. From a commercial point of view, syneresis is typically an undesirable property, and the gels of the present invention desirably, and surprisingly do not exhibit syneresis.

To prepare a gel of the invention, an ester-terminated poly(ester-amide) resin is combined with a liquid. The two ingredients are taken to elevated temperature, e.g., up to about 80–150° C., until the resin completely dissolves in the liquid. A lower temperature may be used if a solution can be prepared at the lower temperature. Upon cooling, the mixture forms the gel of the invention. Preferably, the liquid is a low-polarity liquid as described above, and more preferably the liquid is a hydrocarbon. The liquid may contain more than one component, e.g., hydrocarbon as well as ester-containing material. In any event, the ester-terminated poly(ester-amide) is combined with the liquid such that the weight percent of ETPEA in the ETPEA+solvent mixture is about 5–50%, and preferably is about 10–45%. Such gels may be transparent, translucent or opaque, depending on the precise identities of the ester-terminated poly(ester-amide) and liquid, as well as the concentration of ETPEA in the mixture.

The gels of the invention may be formulated into personal care products according to techniques well known in the art. The gel may be combined with ingredients conventionally incorporated into personal care products such as chelating agents, colorants, emulsifiers, fillers, hardeners, perfumes, strengtheners, water and wax, to name a few. Such additives are well known in the art, and are also set forth in, e.g., the following documents, all incorporated by reference herein in their entirety: U.S. Pat. Nos. 3,255,082 to Barton, U.S. Pat. No. 4,049,792 to Elsnau, U.S. Pat. No. 4,137,306 to Rubino et al., and U.S. Pat. No. 4,279,658 to Hooper et al. See also U.S. Pat. Nos. 3,148,125 and 5,538,718 (describing the formulation of lipstick and other cosmetic sticks). See also European Patent Application Nos. 1 068 855 A1 and 1 068 856 A1, where the disclosure of these two documents is incorporated herein by reference, where these documents provide additional formulation suggestions for incorporating an organic gellant into a cosmetic or other personal care product, where these formulation suggestions may be employed to formulate a corresponding product with the ETPEA gellant of the present invention in place of some or all of the gallants, e.g., the UNICLEAR™ 80 and 100 gellants, disclosed therein.

Personal care products may be prepared from the ETPEA resin of the invention by mixing the various components of the product at an elevated temperature and then cooling in order to form the gelled (solidified) composition. Desirably, any volatile components are added to the mixture at a relatively late stage of the mixing, so as to limit volatilization of the component. Preferably, the liquid and ETPEA gelling agent are mixed and heated so as to fully dissolve the ETPEA in the liquid (e.g., at 80° C.–150° C.). An active ingredient (e.g., active antiperspirant) can be added after the ETPEA fully dissolves, and mixing then takes place. Mixing may continue during cooling, with colorant or other component being added during the cooling stage.

Thus, the present invention provides a personal care product comprising a resin composition prepared by reacting components comprising dibasic acid, diamine, polyol and mono-alcohol, wherein at least 50 equivalent percent of the dibasic acid comprises polymerized fatty acid; and at least 50 equivalent percent of the diamine is ethylene diamine. The personal care product preferably further comprises at least one cosmetically active ingredient and/or at least one dermatologically active ingredient. The personal care product may constitute a composition for the care and/or treatment and/or making-up of keratinous substances. Suitable compositions include makeup products for the lips such as lipstick and lip pencils, and also for the care and/or treatment of the skin, including the scalp and lips, such as care creams applied daily, sunscreen for the lips and skin, makeup products for the skin, body hygiene products such as deodorants in particular as sticks, and to eye makeup products such as eye liners, in particular in the form of a pencil or mascaras, notably in the form of a cake.

In addition, the present invention provides a controlled release composition comprising a volatile component and a resin composition prepared by reacting components comprising dibasic acid, diamine, polyol and mono-alcohol, wherein at least 50 equivalent percent of the dibasic acid is comprises polymerized fatty acid; and at least 50 equivalent percent of the diamine is ethylene diamine.

Further, the ETPEA resins of the present invention may be combined with a suitable solvent so as to form a gel, where the gel in combination with a wick forms a candle. Thus, in one aspect, the present invention provides a candle comprising a wick and a resin composition prepared by reacting components comprising dibasic acid, diamine, polyol and mono-alcohol, wherein (a) at least 50 equivalent percent of the dibasic acid comprises polymerized fatty acid; (b) at least 50 equivalent percent of the diamine comprises ethylene diamine; (c) 10–60 equivalent percent of the total of the hydroxyl and amine equilvalents provided by diamine, polyol and monoalcohol are provided by monoalcohol; and (d) no more than 50 equivalent percent of the total of the hydroxyl and amine equivalents provided by diamine, polyol and monoalcohol are provided by polyol; the candle further comprising a solvent that is gelled by the resin. In one aspect, the candle contains icons. An exemplary icon is a second gelled phase, preferably visually distinct from the gel formed from ETPEA. The icon(s) may be embedded within the candle, or may be on the surface of the candle. The second gelled phase may be, but need not be, ETPEA. In one aspect, the second gelled phase is transparent.

The candle may, in one aspect, contain hydrocarbon, where the hydrocarbon and the ETPEA resin form a gel. The candle may also, in one aspect, contain a fragrance material. Furthermore, the candle may contain an ester.

Methods of using gels to form candles, including wicks, icons, the use of hydrocarbons, suitable fragrance materials, and suitable esters, are well known in the candle-making art, where these methods and components may be used to prepare candles from EPTEA resins.

Again, in regard to the preparation of, and components used in, candles, personal care products, and fragrance-releasing compositions, reference is made U.S. Pat. Nos. 3,615,289, 3,645,705, 6,111,055, 6,129,771 and 6,214,063 (describing the formulation of candles and pigmented objects embedded in candle, which are an example of an "icon"; U.S. Pat. Nos. 3,148,125 and 5,538,718 (describing the formulation of lipstick and other cosmetic sticks); and U.S. Pat. Nos. 4,275,054, 4,937,069, 5,069,897, 5,102,656 and 5,500,209 (describing the formulation of deodorant and/or antiperspirant).

The following examples are set forth as a means of illustrating the present invention and are not to be construed as a limitation thereon.

EXAMPLES

Example 1

ETPEA Resin

The following reactants and relative reactant amounts were used to prepare an ETPEA resin:

| Reactant | Equivalents | Weight Percent |
| --- | --- | --- |
| PRIPOL ™ 1015 dimer acid | 100 | 76.7 |
| Stearyl alcohol | 28 | 17.3 |
| Neopentyl glycol | 16 | 2.0 |
| Ethylenediamine | 56 | 4.0 |

The ETPEA was synthesized by charging the PRIPOL™ 1015 dimer acid, sterary1 alcohol and neopentyl glycol to a reaction vessel at room temperature, heating the mixture to 100° C., adding the ethylenediamine, heating to 220° C. and holding for 3 hours, and holding under vacuum (8–10 mbar) at 220° C. for 2 hours. The ETPEA had a softening point of 76.7° C. and a color of 596 (APHA).

Example 2

ETPEA Resin

The following reactants and relative reactant amounts were used to prepare an ETPEA resin:

| Reactant | Equivalents | Weight Percent |
| --- | --- | --- |
| EMPOL ™ 1008 dimer acid | 100 | 75.8 |
| Stearyl alcohol | 25 | 17.1 |
| Neopentyl glycol | 25 | 3.3 |
| Ethylenediamine | 50 | 3.8 |

The ETPEA was synthesized following the procedure described in Example 1, using the relative reactant amounts set forth in the above Table. The product ETPEA has a softening point of 74.7° C. and a color of 238 (APHA).

Throughout the present specification, where resins or reaction mixtures are described as including or comprising specific components or materials, it is contemplated by the inventors that the resins or reaction mixtures of the present invention also consist essentially of, or consist of, the recited components or materials. Accordingly, throughout the present disclosure any described composition (resin or reaction mixture) of the present invention can consist essentially of, or consist of, the recited components or materials.

All publications and patent applications mentioned in this specification are herein incorporated by reference to the same extent as if each individual publication or patent application was specifically and individually incorporated by reference.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

What is claimed is:

1. A resin composition prepared by reacting components comprising dibasic acid, diamine, polyol and monoalcohol, wherein
    (a) at least 50 equivalent percent of the dibasic acid comprises polymerized fatty acid;
    (b) at least 50 equivalent percent of the diamine comprises ethylene diamine;
    (c) 10–60 equivalent percent of the total of the hydroxyl and amine equilvalents provided by diamine, polyol and monoalcohol are provided by monoalcohol; and
    (d) no more than 50 equivalent percent of the total of the hydroxyl and amine equivalents provided by diamine, polyol and monoalcohol are provided by polyol.

2. A resin composition prepared by reacting components consisting essentially of dibasic acid, diamine, polyol and mono-alcohol, wherein
    (a) at least 50 equivalent percent of the dibasic acid comprises polymerized fatty acid;
    (b) at least 50 equivalent percent of the diamine comprises ethylene diamine;
    (c) 10–60 equivalent percent of the total of the hydroxyl and amine equilvalents provided by diamine, polyol and monoalcohol are provided by monoalcohol; and
    (d) no more than 50 equivalent percent of the total of the hydroxyl and amine equivalents provided by diamine, polyol and monoalcohol are provided by polyol.

3. The resin composition of claim 1 wherein polymerized fatty acid constitutes at least 75 equivalent percent of the acid equivalents of the dibasic acid.

4. The resin composition of claim 1 wherein polymerized fatty acid constitutes at least 90 equivalent percent of the acid equivalents of dibasic acid.

5. The resin composition of claim 2 wherein polymerized fatty acid constitutes at least 90 equivalent percent of the acid equivalents of dibasic acid.

6. The resin composition of claim 1 wherein ethylene diamine constitutes at least 75 equivalent percent of the amine equivalents from diamine.

7. The resin composition of claim 1 wherein polymerized fatty acid constitutes at least 75 equivalent percent of the acid equivalents of the dibasic acid, and ethylene diamine constitutes at least 75 equivalent percent of the amine equivalents of diamine.

8. The resin composition of claim 2 wherein polymerized fatty acid constitutes at least 75 equivalent percent of the acid equivalents of the dibasic acid, and ethylene diamine constitutes at least 75 equivalent percent of the amine equivalents of the amine.

9. The resin composition of claim 1 wherein the monoalcohol reactant comprises an alcohol of the formula $R^3$—OH and $R^3$ is a hydrocarbon.

10. The resin of claim 9 wherein $R^3$ is a $C_{10}$–$C_{30}$ hydrocarbon.

11. The resin of claim 9 wherein $R^3$ is a $C_{30}$–$C_{70}$ hydrocarbon.

12. The resin of claim 1 wherein the monoalcohol is of the formula $R^3$—OH and $R^1$ is an alkyl or aralkyl group.

13. The resin of claim 1 wherein the monoalcohol is selected from decanol, tetradecanol, hexadecanol, octadecanol (stearyl alcohol), behenyl alcohol and linear wax alcohols having about 22–70 carbons.

14. The resin of claim 1 wherein the polyol is of the formula $R^4(OH)_n$ wherein $R^4$ is an n-valent organic group.

15. The resin of claim 14 wherein $R^4$ is a $C_2$–$C_{20}$ organic group without hydroxyl substitution.

16. The resin of claim 14 wherein $R^4$ is a hydrocarbon.

17. The resin of claim 14 wherein n is selected from 2, 3, 4, 5 and 6.

18. The resin of claim 14 wherein the polyol is selected from ethylene glycol, propylene glycol, butylene glycol, glycerol, trimethylolpropane, pentaerythritol, neopentyl glycol, tris(hydroxylmethyl)methanol, di-pentaerythritol, and tri-pentaerthyritol.

19. The resin of claim 1 wherein the amine equivalents from diamine equal 0.3 to 0.75 of the total amine and hydroxyl equivalents provided by diamine, polyol and mono-alcohol.

20. The resin of claim 1 wherein the hydroxyl equivalents from polyol equal 0.05 to 0.45 of the total amine and hydroxyl equivalents provided by diamine, polyol and mono-alcohol.

21. The resin of claim 1 wherein the hydroxyl equivalents from mono-alcohol equal 0.20 to 0.45 of the total amine and hydroxyl equivalents provided by diamine, polyol and mono-alcohol.

22. The resin of claim 1 wherein the amine equivalents from diamine equal 0.30 to 0.75 of the total amine and hydroxyl equivalents provided by diamine, polyol and mono-alcohol; the hydroxyl equivalents from polyol equal 0.05 to 0.45 of the total amine and hydroxyl equivalents provided by diamine, polyol and mono-alcohol; and the hydroxyl equivalents from monoalcohol equal 0.20 to 0.45 of the total amine and hydroxyl equivalents provided by diamine, polyol and monoalcohol.

23. The resin of claim 2 wherein the amine equivalents from diamine equal 0.30 to 0.75 of the total amine and hydroxyl equivalents provided by diamine, polyol and mono-alcohol; the hydroxyl equivalents from polyol equal 0.05 to 0.45 of the total amine and hydroxyl equivalents provided by diamine, polyol and monoalcohol; and the hydroxyl equivalents from mono-alcohol equal 0.20 to 0.50 of the total amine and hydroxyl equivalents provided by diamine, polyol and monoalcohol.

24. The resin of claim 1 wherein the dibasic acid reactant comprises co-diacid selected from 1,4-cyclohexane dicarboxylic acid, isophthalic acid, adipic acid, azeleic acid, sebacic acid, and dodecandioic acid.

25. The resin of claim 1 wherein the diamine reactant comprises co-diamine selected from 1,6-hexanediamine, xylenediamine, 1,2-propanediamine, 2-methylpentamethylenediamine, and 1,12-dodecanediamine.

26. The resin of claim 1 wherein polymerized fatty acid constitutes at least 75 equivalent percent of the acid equivalents of the dibasic acid, ethylene diamine constitutes at least 75 equivalent percent of the amine equivalents of the amine; the amine equivalents from diamine equals 0.30 to 0.75 of the total amine and hydroxyl equivalents provided by diamine, polyol and mono-alcohol; the hydroxyl equivalents from polyol equals 0.05 to 0.45 of the total amine and hydroxyl equivalents provided by diamine, polyol and mono-alcohol; and the hydroxyl equivalents from mono-alcohol equals 0.20 to 0.45 of the total amine and hydroxyl equivalents provided by diamine, polyol and mono-alcohol.

27. The resin of claim 2 wherein polymerized fatty acid constitutes at least 75 equivalent percent of the acid equivalents of the dibasic acid, ethylene diamine constitutes at least 75 equivalent percent of the amine equivalents of the amine; the amine equivalents from diamine equals 0.30 to 0.75 of the total amine and hydroxyl equivalents provided by diamine, polyol and mono-alcohol; the hydroxyl equivalents from polyol equals 0.05 to 0.45 of the total amine and hydroxyl equivalents provided by diamine, polyol and mono-alcohol; and the hydroxyl equivalents from mono-alcohol equals 0.20 to 0.45 of the total amine and hydroxyl equivalents provided by diamine, polyol and mono-alcohol.

28. A method for preparing a resin composition comprising ester-terminated poly(ester-amide), the method comprising reacting w equivalents of hydroxyl from polyol or a reactive equivalent thereof, x equivalents of carboxylic acid from diacid or a reactive equivalent thereof, y equivalents of amine from diamine, and z equivalents of hydroxyl from monoalcohol or a reactive equivalent thereof under reactions conditions to provide a resin composition having an acid number of less than 20 and an amine number of less than 20, wherein at least about 50% of the carboxylic acid equivalents are from polymerized fatty acid, at least about 50% of the amine equivalents are from ethylene diamine, and monoalcohol is substantially the only monofunctional reactant used to form the resin.

29. The method of claim 28 wherein $w/(w+y+z)$ is within the range of about 0.05 to 0.45; $y/(w+y+z)$ is within the range of about 0.25 to 0.75; and $z/(w+y+z)$ is within the range of 0.20 to 0.50.

30. The method of claim 28 wherein 10–60 equivalent percent of the total of the hydroxyl and amine equilvalents provided by diamine, polyol and monoalcohol are provided by monoalcohol; and no more than 50 equivalent percent of the total of the hydroxyl and amine equivalents provided by diamine, polyol and monoalcohol are provided by polyol.

31. The method of claim 28 wherein the resin composition has a softening point within the range of 40 to 150° C.

* * * * *